(12) United States Patent
Rock et al.

(10) Patent No.: US 11,506,646 B2
(45) Date of Patent: Nov. 22, 2022

(54) SENSOR DEVICE FOR DETECTING A PERMANENT GAS

(71) Applicant: SENSIRION AG, Staefa ZH (CH)

(72) Inventors: Frank Rock, Staefa ZH (CH); Werner Hunziker, Staefa ZH (CH)

(73) Assignee: SENSIRION AG, Staefa ZH (CH)

( * ) Notice: Subject to any disclaimer, the term of this patent is extended or adjusted under 35 U.S.C. 154(b) by 564 days.

(21) Appl. No.: 16/476,876

(22) PCT Filed: Jan. 10, 2018

(86) PCT No.: PCT/EP2018/050560
§ 371 (c)(1),
(2) Date: Jul. 10, 2019

(87) PCT Pub. No.: WO2018/130570
PCT Pub. Date: Jul. 19, 2018

(65) Prior Publication Data
US 2019/0353628 A1    Nov. 21, 2019

(30) Foreign Application Priority Data

Jan. 10, 2017 (EP) .................................... 17150906

(51) Int. Cl.
*G01N 33/00* (2006.01)

(52) U.S. Cl.
CPC ....... *G01N 33/0014* (2013.01); *G01N 33/004* (2013.01); *G01N 33/005* (2013.01); *G01N 33/0047* (2013.01)

(58) Field of Classification Search
None
See application file for complete search history.

(56) References Cited

U.S. PATENT DOCUMENTS 3,919,369 A * 11/1975 Holden .............. B01J 20/28042
264/156
6,248,682 B1  6/2001 Thompson et al.
(Continued)

FOREIGN PATENT DOCUMENTS

CN    1994519 A   7/2007
CN  102698505 A  10/2012
(Continued)

OTHER PUBLICATIONS

Database WPI, Week 201681, Thomson Scientific, London, GB; AN 2016-73846X.
(Continued)

*Primary Examiner* — Daniel S Larkin
(74) *Attorney, Agent, or Firm* — JMB Davis Ben-David

(57) ABSTRACT

The invention relates to a sensor device (1) for detecting a gas (G), particularly a permanent gas such as $H_2$, CO, $CO_2$, $CH_4$, comprising: an adsorption filter (30) comprising a body (2) consisting of a molecular sieve material, a sensing element (10) for detecting said gas (G), and a carrier (4) for carrying the sensing element (10), wherein the carrier (4) comprises an opening (50) via which said gas (G) to be detected can reach the sensing element (10), and wherein the adsorption filter (30) is connected, particularly glued, to the carrier (4) and closes said opening (50) so that said gas (G) to be detected can diffuse through said body (2) towards the sensing element (10).

8 Claims, 6 Drawing Sheets

(56) References Cited

U.S. PATENT DOCUMENTS

| | | | |
|---|---|---|---|
| 6,936,147 B2 * | 8/2005 | Prohaska | G01N 27/4045 204/432 |
| 7,491,547 B1 | 2/2009 | Warburton | |
| 8,852,513 B1 | 10/2014 | Speer et al. | |

FOREIGN PATENT DOCUMENTS

| | | | |
|---|---|---|---|
| EP | 2913667 | | 9/2015 |
| JP | S61159146 | | 7/1986 |
| JP | H10177002 | | 6/1998 |
| JP | 2016-200547 | * | 12/2016 |
| JP | 2016200547 | | 12/2016 |
| WO | 20180083130 | | 5/2018 |

OTHER PUBLICATIONS

Database WPI, Week 199836, Thomson Scientific, London, GB; AN 1998-423252.

* cited by examiner

SENSOR DEVICE FOR DETECTING A PERMANENT GAS

CROSS-REFERENCE TO RELATED APPLICATIONS

This is the U.S. National Stage of International Patent Application No. PCT/EP2018/050560 filed Jan. 10, 2018, which was published in English under PCT Article 21(2), and which in turn claims the benefit of European Patent Application No. 17150906.0 filed Jan. 10, 2017.

BACKGROUND OF THE INVENTION

The present invention relates to a sensor device for detecting a gas, particularly a permanent gas such as $H_2$, CO, $CO_2$, or $CH_4$.

The performance of such gas sensor devices for permanent gases can be improved by the use of adsorption filters. Therefore, manufacturers are using adsorption materials that are placed in front of the sensing element. These filters can be powders, small granules or foams. Available solutions are defined by following characteristics: The adsorption material is fixed mechanically, its density is increased by pressing, and the shape of the adsorption body is defined by its housing.

Disadvantageously, using a powder based adsorption filter, the packaging volume can increase by significant factors making miniaturization difficult. Furthermore, the powder-like adsorption materials require a complex processing.

Based on the above, the problem to be solved by the present invention is to provide an improved sensor device of the afore-mentioned kind which requires only a relatively small installation space and particularly avoids problems encountered with dusty powder-like filter materials.

This problem is solved by a sensor device according to the present invention.

Preferred embodiments of this aspect of the present invention are stated in the corresponding sub claims and are further described below.

SUMMARY OF THE INVENTION

The sensor device according to the invention is configured for detecting a gas, particularly a permanent gas such as $H_2$, CO, $CO_2$, or $CH_4$, and comprises:
- an adsorption filter comprising a dimensionally stable body consisting of a molecular sieve material (i.e. the body forms a molecular sieve), wherein said body comprises a diameter in the range from 0.2 mm to 5 mm;
- a sensing element for detecting said gas;
- a carrier for carrying the sensing element, wherein the carrier comprises an opening via which said gas to be detected can reach the sensing element so as to interact with the sensing element and to be detected by the sensing element; and wherein
- the adsorption filter is connected to the carrier and closes said opening so that said gas to be detected can diffuse through said body towards the sensing element.

Particularly, the adsorption filter is connected to the carrier and closes said opening so that said gas to be detected can only diffuse through said body towards the sensing element.

The adsorption filter can be connected to the carrier using a glue, or in form-fitting or force fitting manner, or any combination thereof.

Particularly, according to an embodiment, the adsorption filter is glued to the carrier and closes said opening so that said gas to be detected can only diffuse through said body towards the sensing element.

Particularly, according to an embodiment of the present invention, said body comprises a diameter in the range from 0.5 mm to 3 mm most preferably 1 mm to 2 mm. Particularly, this diameter extends along the extension plane of the carrier or adsorption filter plate (see also below).

In case the body comprises a non-spherical shape, said diameter specified above can be the largest or smallest diameter of the body or an average of said largest and smallest diameter.

Further particularly, the body or adsorption filter can have a thickness (e.g. perpendicular to the direction of said diameter) in the range from 0.1 mm to 5 mm, preferably 0.1 mm to 2 mm.

Further, according to a further embodiment of the present invention, said adsorption filter comprises merely a single body of said molecular sieve material.

Furthermore, generally, it is also possible that the adsorption filter comprises a number of such bodies, particularly less than 20 bodies, particularly less than 10 bodies, particularly less than 5 bodies. The adsorption filter is then also glued to the carrier and closes said opening such that the gas to be detected can then diffuse through one, several or all of said bodies towards the sensing element.

Particularly, as already mentioned above, the body is dimensionally stable according to an embodiment, i.e., the molecular sieve material forming the body does not need an enclosure for the body to maintain its shape. In other words, the molecular sieve material is processed such that the body is a dimensionally stable (e.g. monolithic) body.

Further, according to a further embodiment of the present invention, said body is one of: a body having a convex shape, a bead, a section of a bead, a pellet, a plate.

Particularly, said section of a bead can be generated when surfaces of the adsorption filter plate that has a bead embedded therein are processed (e.g. cut or processed by an abrasive treatment such as grinding) and thereby parts of the body are leveled and then form areas of the outer surfaces of the plate.

Further, according to an embodiment of the present invention, the molecular sieve material is one of or comprises on of: a zeolite, a silica gel, clay, activated carbon, a polymer adsorbent, an aromatic polyimide (e.g. Matrimid® 5218), polyether ether ketone (PEEK), a perfluoropolymer (e.g. Teflon AF2400 (Du Pont), Hyflon AD 40/60 (Solvay), Cytop (Asahi Glass)), poly(2,6-diphenylphenylene oxide) (e.g. Tenax TA, Tenax GR), cellulose acetate.

Further, according to an embodiment of the present invention, the body is arranged or embedded in a form fitting manner (particularly with an adhesive bond) in a material of the adsorption filter. Thus, particularly, said material encapsulates the body laterally such that the body extends from the front side to the back side of the adsorption filter plate and forms a flow path through the carrier material. It is also possible that an end region of the embedded body or two opposing end regions of the body protrude out of said material of the adsorption filter.

Further, according to an embodiment of the present invention, the carrier material comprises a cured resin, particularly epoxy, PU, or an acrylate. Other resins or curable materials are also conceivable.

Further, according to an embodiment of the present invention, the adsorption filter is an adsorption filter plate, wherein the body and the carrier material form said plate, and wherein said adsorption filter plate comprises a front side and an opposing back side.

According to an embodiment the front side and/or the back side is planar.

Alternatively, according to an embodiment, an end region of the body protrudes out of said material of the carrier at the front side, so that the front side is non-planar.

Further, according to an embodiment, a further end region of the body protrudes out of said material of the carrier at the back side, so that the back side is non-planar.

Further, the body may also be flush with the material at the front side and/or back side.

Further, according to an embodiment, the front side and the back side extend parallel to each other.

Particularly, the shape of the front and/or back side, particularly said planar front and/or back side may be achieved by additional processing steps such as cutting or grinding of the respective front side.

Furthermore, in an embodiment, the back side of the adsorption filter plate may comprise at least one recess, that particularly engages with a corresponding protrusion of the front side of the carrier, particularly in a form-fitting and/or force fitting manner. Furthermore, according to an embodiment, the back side of the adsorption filter plate may comprise at least one protrusion that particularly engages with a corresponding recess of the front side of the carrier, particularly in a form-fitting and/or force fitting manner. Furthermore, the back side may comprise several such recesses and/or protrusions.

Further, according to an embodiment of the present invention, the body extends inside the adsorption filter plate from the front side to the back side of the adsorption filter plate and thus forms a passage for the gas to be detected, which passage extends through the whole adsorption filter plate, wherein a front side of the body forms an area of said front side of the plate, and wherein a back side of the body forms an area of said back side of the plate. Said areas may be obtained or processes by means of said cutting or grinding (or by means of other processing steps). However, said areas of the body, particularly at the front side of the adsorption filter plate, do not need to be flush with a surface of the embedding material of the adsorption filter plate.

Further, according to an embodiment of the present invention, the carrier comprises a front side, particularly a planar front side, in which a recess is formed, wherein the sensing element is arranged in said recess, and wherein the recess comprises said opening that e.g. extends in the plane of the planar front side of the carrier. In other words, said recess is accessible via said opening.

Further, according to an embodiment of the present invention, the adsorption filter plate is glued and/or otherwise connected (e.g. in form-fitting and/or force-fitting manner) to the carrier (particularly the adsorption filter can be glued with its back side to the front side of the carrier), particularly such that a gas-tight seal is established between said material of the adsorption filter plate and the carrier, so that the gas to be detected can diffuse, particularly only diffuse, via said body through the adsorption filter plate to reach the sensing element.

Further, according to an embodiment of the present invention, said body covers said opening of the recess of the carrier. Particularly, said area formed by the back side of the body is arranged in front of said opening and particularly covers the opening. Particularly, said area may comprise a circumferential outer section that is glued to a boundary region of the front side of the carrier, which boundary region surrounds said opening.

Optionally, a transfer support is used for achieving an improved handling and/or a mechanical stability.

In a preferred embodiment, the adsorption filter plate (or the corresponding material) is fixed on a transfer support (e.g. after a processing of the front and/or back side of the adsorption filter plate as described e.g. herein). In a preferred embodiment, the transfer support is based on or made of polyester. In one embodiment, the transfer support is removed after attachment of the adsorption filter plate to the carrier, before or after separating the carrier (and particularly components thereon) into individual sensor devices or groups of sensor devices. According to an embodiment, the transfer support can be a gas permeable transfer support (particularly permeable for the respective target gas that is to be detected). Particularly in case the transfer support remains on the structure/sensor device. Such a gas permeable sensor support can comprise or can be made of a mesh, a scrim, a metallic grid etc. Further, in an embodiment, particularly in case the transfer support remains on the sensor device/forms a permanent component of the sensor device, the transfer support is arranged on the front side of the adsorption filter plate.

Further, according to another embodiment of the present invention, the carrier forms a housing enclosing an internal space of the carrier, wherein the sensing element is arranged at least in sections (or completely) in said internal space, and wherein the body is glued to the carrier such that the body rests inside the internal space in front of the opening.

Further, according to a further aspect of the present invention, a method for producing a sensor device is disclosed, wherein a plurality of (e.g. dimensionally stable) bodies formed out of a molecular sieve material (i.e. each body forms a molecular sieve) is arranged in a two-dimensional plane (e.g. in equidistant intervals, e.g. according to a checkered pattern), wherein a free space between the bodies is filled with a material that is cured, wherein an adsorption filter plate is formed in which the bodies are embedded in the material and each body extends from a front side of said adsorption filter plate to a back side of said adsorption filter plate, and wherein each body is arranged in front of an associated sensing element (or associated thereto) for forming a corresponding number of sensor devices.

Particularly, the individual sensor devices are separated from one another (e.g. to get single sensor devices).

Particularly, according to an embodiment, the bodies all have the same diameter, and/or surface area, and/or volume.

However, according to an embodiment, at least two of the bodies, several of the bodies or all of the bodies have a different diameter, and/or surface area, and/or volume.

Particularly, in an embodiment, the adsorption filter plate can be processed on its front side (facing away from the carrier) and/or on its back side, e.g. to achieve a desired thickness and/or shape (particularly flatness) of the respective side/plate and/or bodies and/or to adjust the diameter of said areas formed by the bodies, through which areas the gas to be detected passes towards the sensing element (see also above).

Particularly, in an embodiment, the material is filled into said free space between the bodies such that all bodies are completely covered at the front side of the adsorption filter plate. Particularly, material covering the bodies at the front side is then removed (e.g. after curing of the material) in order to expose the bodies, wherein particularly also sections of the bodies can be removed, so that the bodies extend up to the front side and form part of the front side of the adsorption filter plate (e.g. after said removal of excess material at the front side).

Alternatively, in an embodiment, the material is filled into said free space between the bodies such that at least one body, several bodies or all bodies protrude out of the material at the front side of the adsorption filter plate. Particularly, a region of the respective body that protrudes out of the material can be removed, e.g. in order to get a flat front side or a desired shape of the front side of the adsorption filter plate. Particularly, in certain embodiments, the step of arranging each body in front of an associated sensing element for forming a corresponding number of sensor devices corresponds to one of the following possibilities/embodiments:

- separating said adsorption filter plate into a plurality of adsorption filter plate sections, wherein each section comprises one of said bodies, and arranging each of said adsorption filter plate sections on an associated carrier comprising a sensing element for forming a corresponding sensor device, or
- separating said adsorption filter plate into a plurality of adsorption filter plate sections, wherein each section comprises one of said bodies, and arranging each of said adsorption filter plate sections on a single carrier (i.e. on the same carrier) comprising a corresponding number of sensing elements so that each body is associated to (e.g. arranged in front of) an associated sensing element, and separating the single carrier with the attached adsorption filter plate sections into a plurality of individual sensor devices (each comprising a body and a sensing element), or
- arranging said adsorption filter plate on a single carrier comprising a corresponding number of sensing elements so that each body is associated to (e.g. arranged in front of) an associated sensing element, and separating the single carrier with the attached adsorption filter plate into a plurality of individual sensor devices (each comprising a body and a sensing element).

According to yet another aspect of the present invention, another method for producing a sensor device is disclosed, wherein a plurality of (e.g. dimensionally stable) bodies formed out of a molecular sieve material (i.e. each body forms a molecular sieve) is arranged on a single carrier that comprises a plurality of sensing elements so that each body is associated to (e.g. arranged in front of) one of the sensing elements, wherein a free space between the bodies is filled with a material that is cured so that an adsorption filter plate is formed that is connected to the single carrier (e.g. glued to the single carrier or connected to the single carrier in a form-fitting and or force-fitting manner), and wherein the carrier with the attached adsorption filter plate is separated into a plurality of individual sensor devices (each comprising a body and a sensing element).

Optionally, the front side of the adsorption filter plate (which front side faces away from the carrier) is processed to achieve a desired thickness and/or shape (particularly flatness) of the front side/plate and/or bodies and/or to adjust the diameter of said areas on the front side formed by the bodies through which areas the gas to be detected passes towards the sensing element (see also above).

Particularly, in an embodiment, the material is filled into said free space between the bodies such that all bodies are completely covered at the front side of the adsorption filter plate. Particularly, material covering the bodies at the front side is then removed (e.g. after curing of the material) in order to expose the bodies, wherein particularly also sections of the bodies can be removed, so that the bodies extend up to the front side and form part of the front side of the adsorption filter plate (e.g. after said removal of excess material at the front side).

Alternatively, in an embodiment, the material is filled into said free space between the bodies such that at least one body, several bodies or all bodies protrude out of the material at the front side of the adsorption filter plate. Particularly, a region of the respective body that protrudes out of the material can be removed, e.g. in order to get a flat front side or a desired shape of the front side of the adsorption filter plate.

According to yet another aspect of the present invention, a method for producing a sensor device is disclosed wherein a plate-shaped body formed out of a molecular sieve material is arranged on a single carrier that comprises a plurality of sensing elements, wherein molecular sieve material of the plate-shaped body is removed around each sensing element to form separate adsorption filter bodies, wherein each adsorption filter body is associated to (e.g. arranged in front of) one of the sensing elements, and wherein a free space between said bodies is filled with a material that is cured to seal the respective adsorption filter body to the carrier, and wherein the carrier with the attached adsorption filter bodies is separated into a plurality of individual sensor devices (each comprising a body and a sensing element).

Also here, optionally, the front side of the adsorption filter plate (which front side faces away from the carrier) formed by the adsorption filter bodies and the material filled in between said bodies can be processed to achieve a desired thickness and/or flatness of the adsorption filter plate/layer and/or bodies and to adjust the diameter of said areas on the front side formed by the bodies, through which areas the gas to be detected passes towards the sensing element (see also above).

Generally, in the methods described above, the bodies can be arranged on a substrate for arranging the bodies in said two-dimensional plane described above. This substrate can form the transfer support described above. The transfer support can also be provided in addition to the substrate and is then attached to the substrate, particularly arranged below the substrate on a side facing away from the adsorption filter plate. The transfer support can be a permanent component of the sensor device and is then permeable for the respective gas to be detected and is preferably arranged on the front side of the adsorption filter plate. The transfer support can be formed out of or comprise one or several of the materials already described above.

According to yet a further aspect of the present invention, a sensor device for detecting a gas is disclosed, comprising: an adsorption filter comprising a body consisting of a molecular sieve material, a sensing element for detecting said gas, a carrier for carrying the sensing element, wherein the carrier comprises an opening via which said gas to be detected can reach the sensing element, and wherein the adsorption filter is connected or glued to the carrier and closes said opening so that said gas to be detected can diffuse through said body towards the sensing element.

This aspect of the present invention can also be further characterized using the features described herein, particularly as stated in the sub claims.

BRIEF DESCRIPTION OF THE DRAWINGS

Further features, advantages and embodiments of the present invention will be described below with reference to the Figures, wherein

FIG. 1 shows three sensor devices according to the invention in a cross sectional view (upper part) and as well as top view of these sensors 1. The sensor devices can be produced using one of the methods described herein. Particularly, the shown three sensors 1 may be produced as a single component and may then be separated into individual sensor devices 1.

Figure 1:
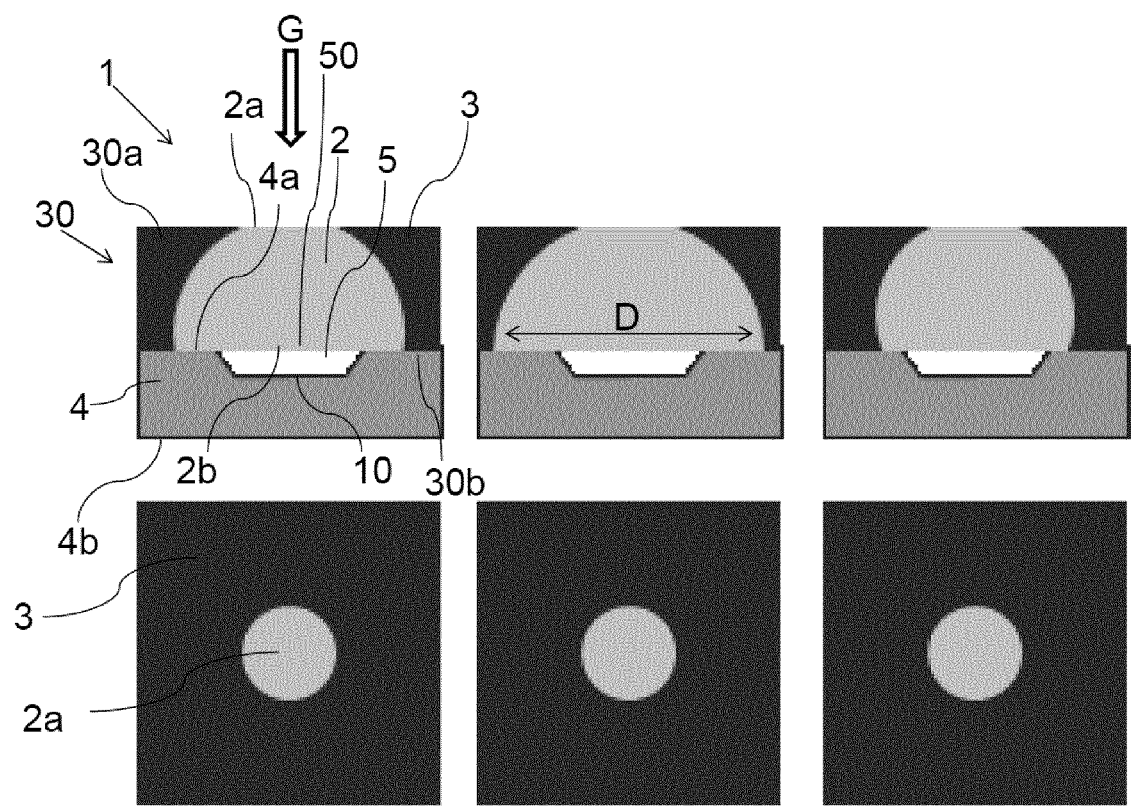
FIG. 1 shows a cross sectional view of three sensor devices according to the invention (upper row), and a top view of said sensor devices (lower row)

In the following a single sensor device 1 shall be described. Particularly, the sensor device 1 is configured for detecting the presence of a gas in the vicinity of the sensor device 1, particularly a permanent gas such as $H_2$, CO, $CO_2$, $CH_4$. For this, the sensor device 1 comprises an adsorption filter 30 comprising a particularly dimensionally stable body 2 consisting of a molecular sieve material, and a sensing element 10 for detecting said gas G. Sensing elements 10 that are suitable for detecting said gases G are known in the state of the art. The filter 30 serves for filtering other gaseous components that disturb the detection process or produce signals that shall be suppressed.

The sensor device 1 further comprises a carrier 4 for carrying the sensing element 10, wherein the carrier 4 comprises an opening 50 via which said gas G to be detected can reach the sensing element 10 so as to interact with the sensing element 10 and be detected by the sensing element 10.

Further, the adsorption filter 30 is glued to the carrier 4 and thereby closes said opening 50 so that said gas G to be detected can diffuse through said body 2 towards the sensing element 10. Thus, a gas-tight seals extends around the opening 50 between the filter 30 and the carrier 4.

As shown in FIG. 1, the body 2 is embedded in a form fitting manner (particularly with an adhesive bond) in a carrier material 3 of the adsorption filter 30, e.g. by means of potting, molding or the like. Particularly, said carrier material can be a fluid epoxy resin which is eventually cured to form an adsorption filter plate 30.

Particularly, this adsorption filter plate 30 that is formed by the body 2 and the carrier material 3 encapsulating the latter, comprises a planar front side 30a and an opposing planar back side 30b, which back side 30b runs parallel to the front side 30a. Furthermore, the embedded body 2 extends inside the adsorption filter plate from the front side 30a to the back side 30b and thus forms a passage of flow path for the gas G to be detected through the adsorption filter plate 30. As further shown in FIG. 1, a front side 2a of the body 2 is flush with said front side 30a of the adsorption filter plate 30 and thus forms an area of said front side 30a, and a back side 2b of the body 2 is flush with the back side 30b and forms an area of said back side 30b of the adsorption filter plate 30. The sizes of these areas can be adjusted by shaping the front and back side 30a, 30b correspondingly (e.g. by cutting or grinding or other processes).

Furthermore, the carrier 4 comprises a planar front side 4a in which a recess 5 is formed, wherein the sensing element 10 is arranged in said recess 5 (e.g. on the bottom of the recess 5). Further, the sensing element 10 may fill said recess 5 completely. The recess 5 further comprises said opening 50, which opening 50 extends in the plane of the planar front side 4a of the carrier 4.

In order to achieve a gas tight seal between the carrier 4 and the plate 30, the adsorption filter plate 30 is glued with its back side 30b to the front side 4a of the carrier 4 so that the gas G to be detected can diffuse via said body 2 through the adsorption filter plate 30 to reach the sensing element 10 mounted on the carrier 4.

Particularly, for achieving said gas-tight seal, the body 2 covers said opening 50 of the recess 5 of the carrier 4, wherein particularly said area 2b comprise a circumferential outer section that is glued to a boundary region of the front side 4a of the carrier 4, which boundary region 4c surrounds said opening 50.

Figure 3:
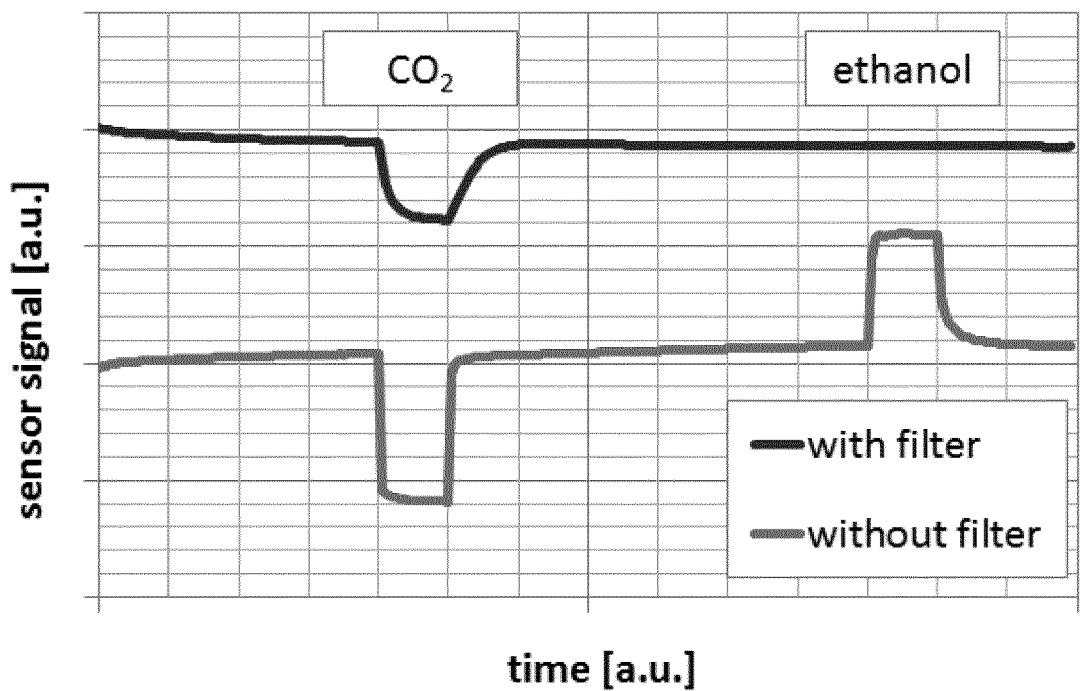
FIG. 3 shows a sensor signal of a sensor device for detecting a permanent gas with adsorption filter according to the invention (upper signal) and without adsorption filter (lower signal)

As an example, FIG. 3 shows sensor signals for a sensor device 1 according to the invention for detecting $CO_2$ as gas G. Particularly, the absorption filter 30 was prepared as described above with a 2 mm 13× zeolite bead and its thickness reduced to 700 µm by grinding. As can be seen, the sensor 1 is not sensitive to ethanol anymore, and the response time to $CO_2$ is only slightly decreased.

Figure 2:
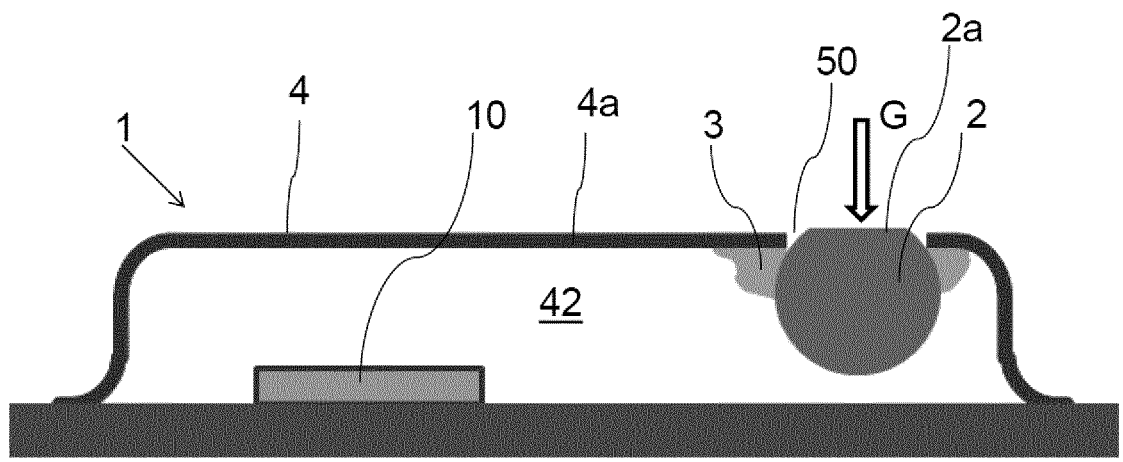
FIG. 2 shows a further embodiment of a sensor device according to the invention.

Furthermore, FIG. 2 shows an alternative embodiment of the present invention. Here, the carrier 4 forms a housing enclosing an internal space 42, wherein the sensing element 10 is now arranged in said internal space 42. Particularly, the body 2 is a leveled bead 2 that is glued to the carrier 4 using a glue material 3 such that the body 2 is arranged inside the internal space 42 and closes an opening 50 of the housing 4 formed in a top side 4a of the housing. Particularly, the leveled front side 2a of the body 2 is flush with said top side 4a of the housing 4.

Finally, FIGS. 4 to 8 show an exemplary method for producing a sensor device 1, particularly several sensor devices 1 in parallel, according to the present invention.

Figure 4:
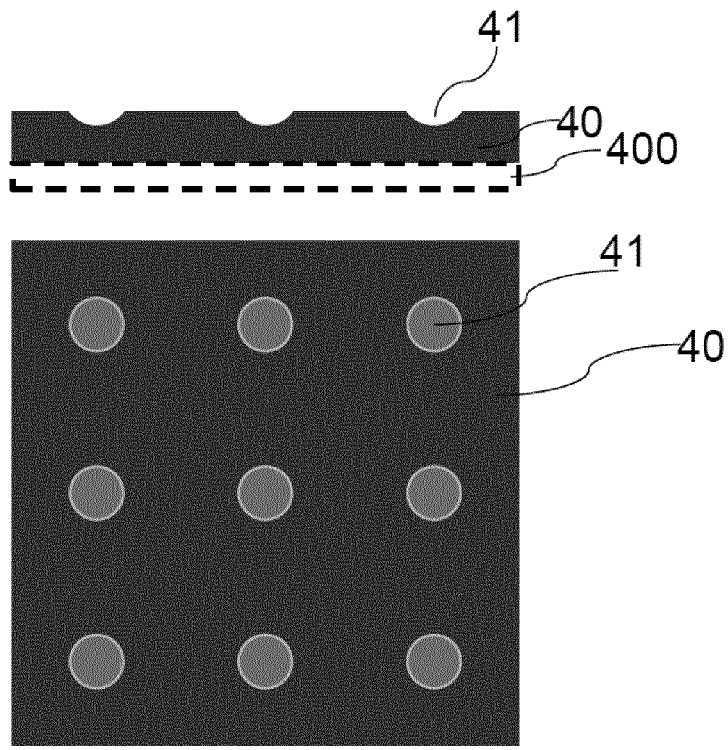
FIGS. 4 to 8 show an exemplary process for producing a sensor device according to the present invention.
Figure 5:
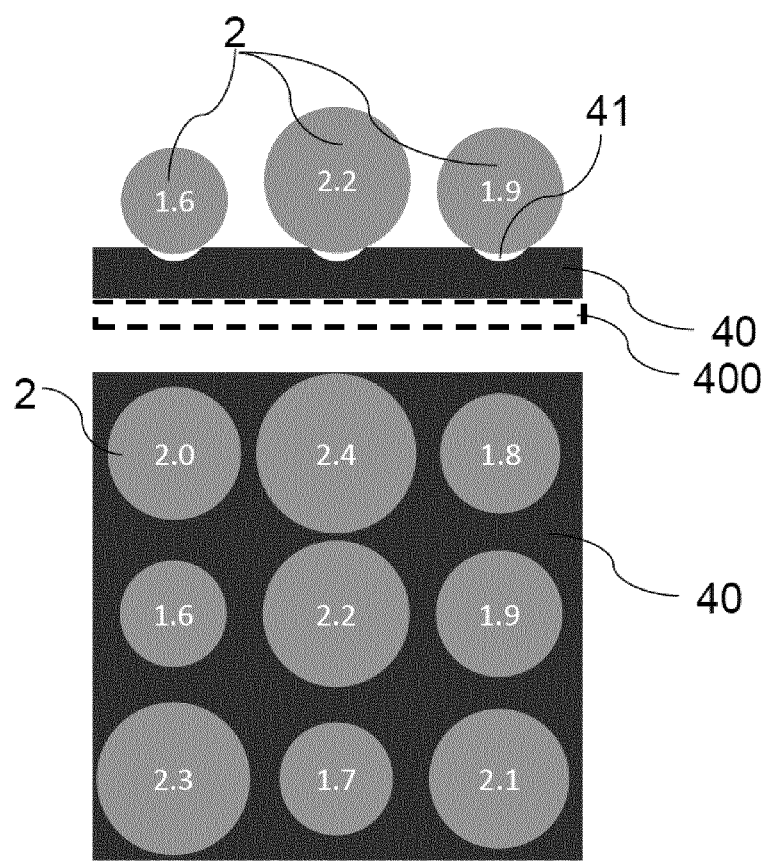

For this, a plurality of dimensionally stable bodies 2, here in the form of spheres having particularly different diameters and formed out of a molecular sieve material (i.e. each body forms a molecular sieve) is arranged in a two-dimensional plane (e.g. in equidistant intervals, e.g. according to a checkered pattern) by placing each body 2 on an associated recess 41 formed into a substrate 40 as shown in FIGS. 4 and 5.

Figure 6:
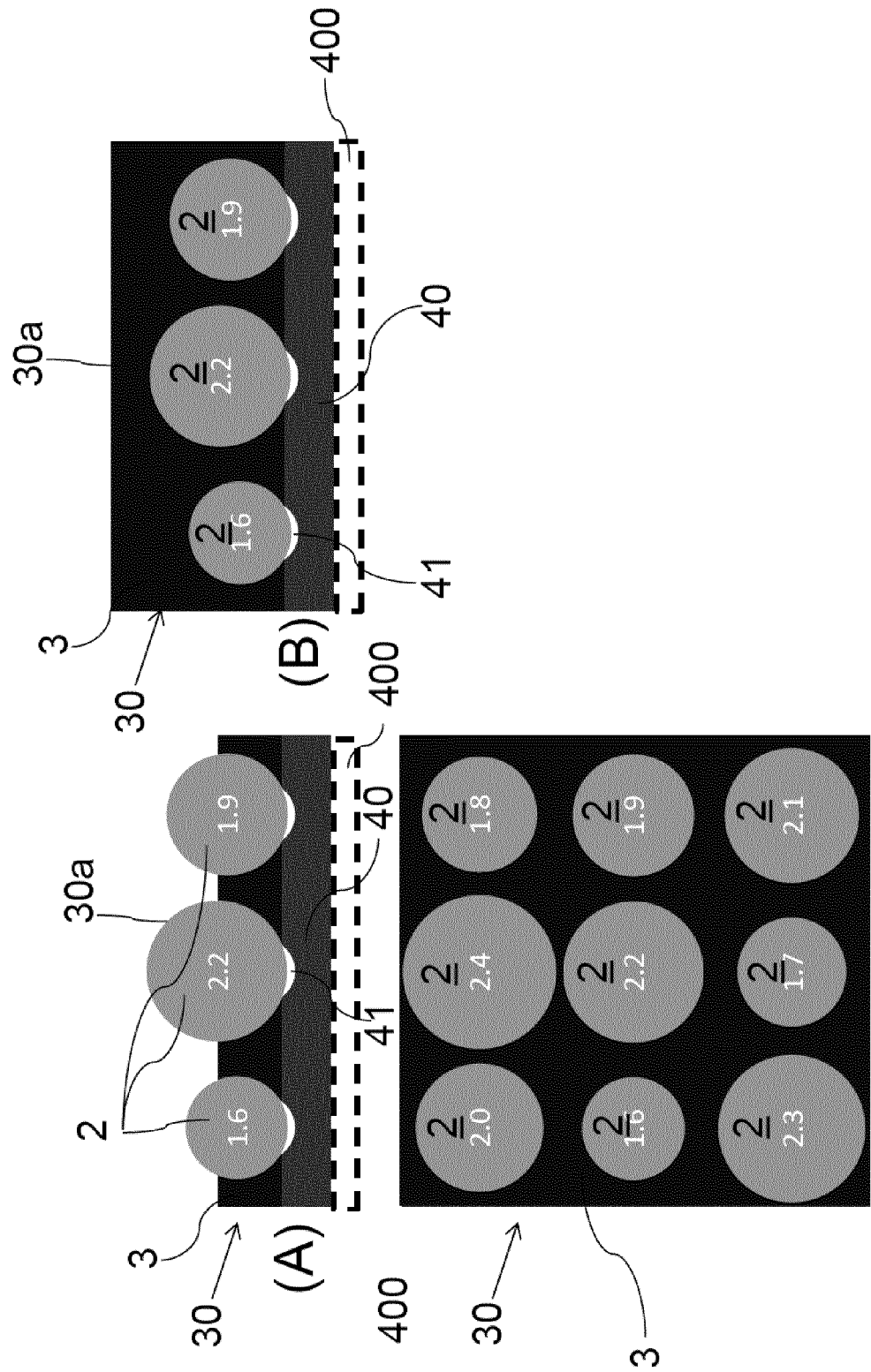

Further, as can be seen in FIG. 6, a free space between the bodies 2 arranged on the substrate 40 is filled with a material 3 that is then cured, wherein an adsorption filter plate 30 is formed in which the bodies 2 are embedded in the material 3 and each body 2 extends from a front side 30a of said adsorption filter plate 30 to a back side 30b of said adsorption filter plate 30 as shown in FIG. 6(A), where the bodies protrude out of the material 3. Particularly, the substrate 40 can also form a transfer support for better handling of the adsorption filter plate 30 (see below) and for providing mechanical stabilization of the adsorption filter plate, particularly in case the adsorption filter plate 30 is relatively thin. Such a transfer support can remain on the sensor device or may be removed later on, e.g. after connecting the filter plate 30 to the carrier 4. As shown e.g. in FIGS. 4 to 6 also a separate transfer support 400 (in addition to substrate 40) may optionally be used to improve handling/mechanical stability of the filter plate 30. In case the transfer support 40, 400 remains on the sensor device, the transfer support is preferably arranged on the front side 30a of the adsorption filter plate 30 (cf. e.g. FIG. 7) and is then particularly configured to be permeable for the gas G that is to be detected. A transfer support 400 can also be applied/connected to the adsorption filter plate after the surfaces of the filter plate have been processed (cf. e.g. FIG. 7).

Further, the bodies 2 can also be completely covered with the material 3 at the front side as shown in FIG. 6(B).

Figure 7:
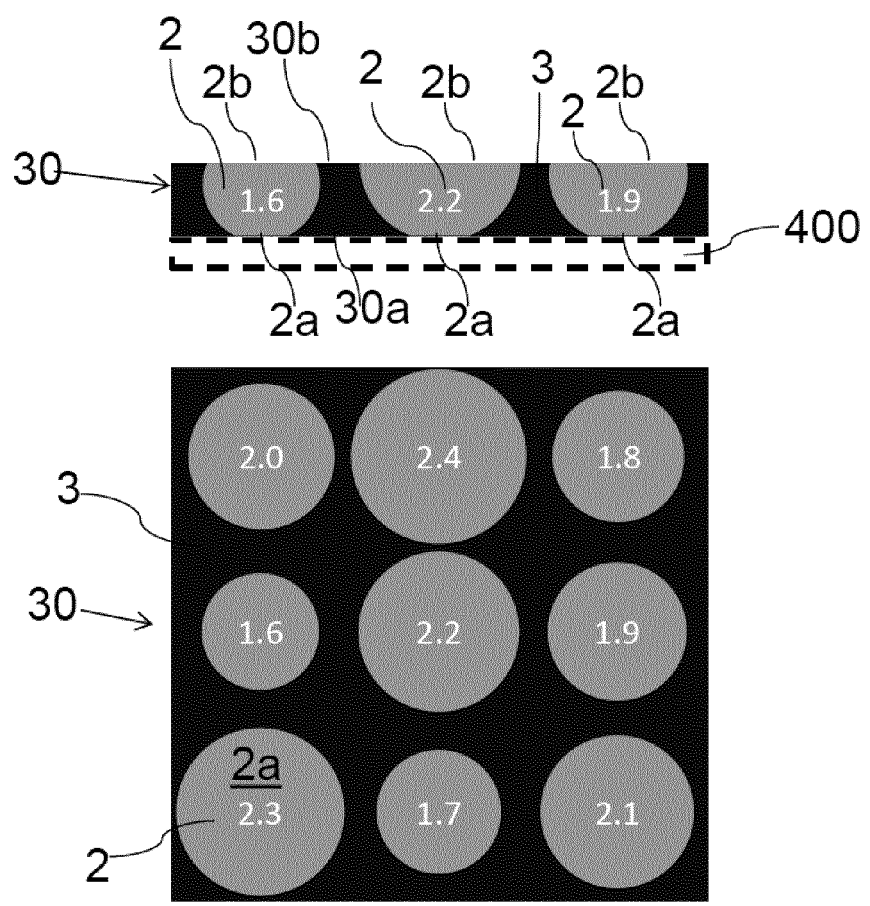

Particularly, in both cases (complete filling or only partial filling of said free space between the bodies 2 with said material), the front side 30a of the adsorption filter plate 30 can be processed, e.g. by grinding or cutting, to achieve a flat front side 30a as shown in FIG. 7. Further, the plate 30 can be removed from the substrate 40 and also the back side 30b can be processed, e.g. by grinding or cutting, for achieving a flat back side 30b of the adsorption filter plate 30 such that the bodies 2 of the plate 30 extend from its front side 30a, where an area 2a of the respective body 2 forms a part of said front side 30a, to the back side 30b, where an area 2b of the respective body 2 forms a part of said back side 30b. Thus gas G can pass the plate 3 via the bodies 2 by entering via said areas 2a and leaving the plate 30 via said areas 2b.

Figure 8:
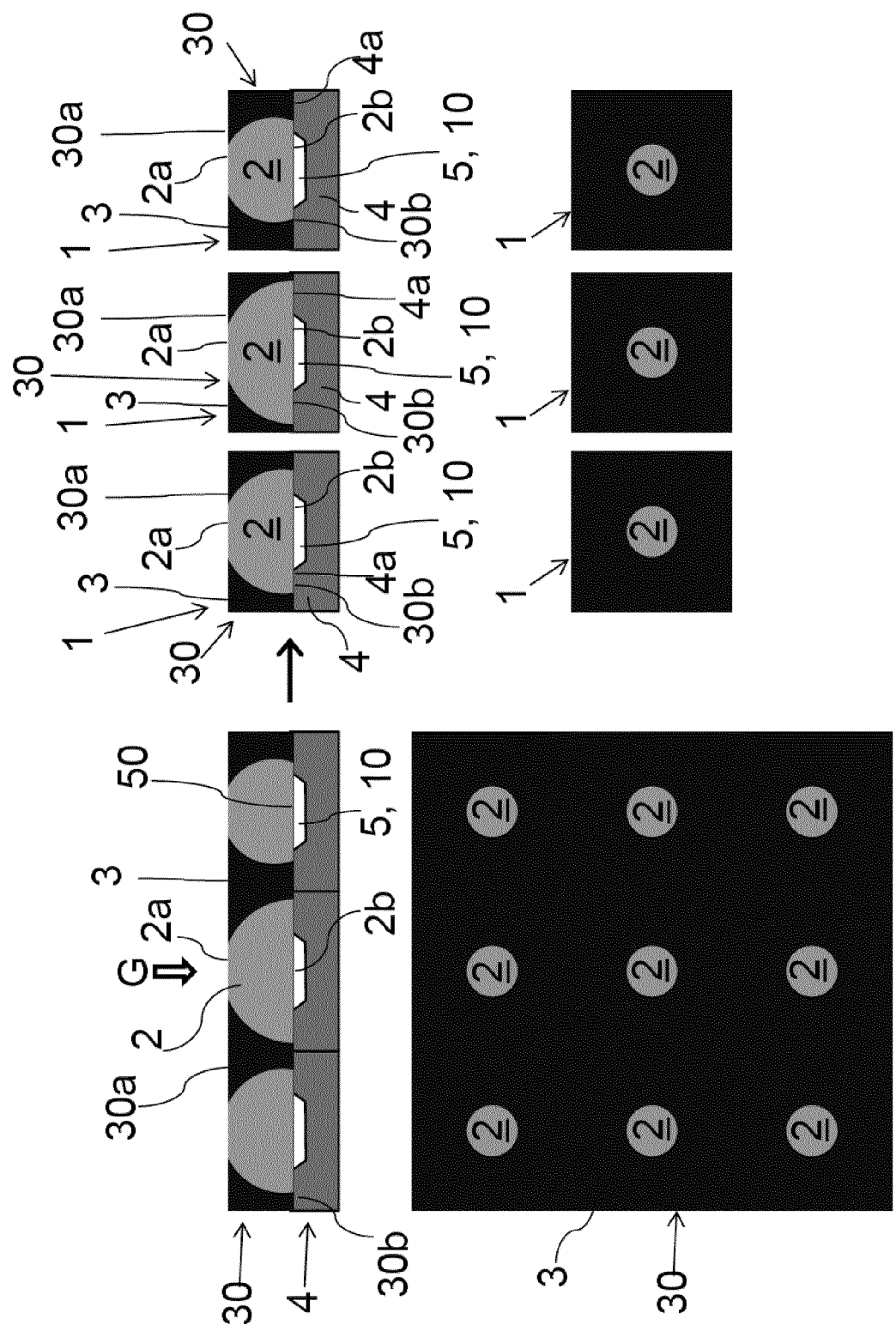

Further, the adsorption filter plate 30 is arranged on a carrier 4 comprising a plurality of recesses 5 with openings 50 wherein a sensing element 10 for detecting said gas G is arranged in each recess 5, and wherein the plate 30 is arranged such on the carrier 4 that each body 2 is associated to one sensing element 10, particularly such that the area 2b of the respective body 2 covers its associated recess 5 as shown in FIG. 8. Here, the material 3 of the plate 30 may be glued to a front side 4a of the carrier, in which front side 4a said recesses 5 receiving the sensing elements 10 are formed. In this way a seal is established around each recess 5 and gas can only enter the respective recess 5 via the respective body 2 that is formed out of said molecular sieve material.

After having connected the plate 30 to the carrier 4, this assembly can be separated into individual sensor devices 1 wherein each sensor device comprises a body 2 as a passage to a sensing element 10 as shown in FIG. 8 on the right hand side.

Alternative production methods are described above.

The invention claimed is:

1. A sensor device (1) for detecting a gas (G), comprising:
an adsorption filter (30) comprising a body (2) consisting of a molecular sieve material, wherein said body comprises a diameter (D) in the range from 0.2 mm to 5 mm;
a sensing element (10) for detecting said gas (G); and
a carrier (4) for carrying the sensing element (10), wherein the carrier (4) comprises an opening (50) via which said gas (G) to be detected can reach the sensing element (10); and
wherein
the adsorption filter (30) is connected to the carrier (4) and closes said opening (50) so that said gas (G) to be detected can diffuse through said body (2) towards the sensing element (10), wherein the adsorption filter (30) is an adsorption filter plate (30), wherein the body (2) is embedded in a form fitting manner in a cured material (3) of the adsorption filter (30), and wherein said adsorption filter plate (30) comprises a front side (30a) and an opposing back side (30b), wherein the body (2) extends inside the adsorption filter plate from the front side (30a) to the back side (30b) of the adsorption filter plate (30) and thus forms a passage for the gas (G) to be detected through the adsorption filter plate (30), wherein a front side (2a) of the body (2) forms an area of said front side (30a) of the adsorption filter plate (30), and wherein a back side (2b) of the body (2) forms an area of said back side (30b) of the adsorption filter plate (30), and wherein the body is flush with the cured material (3) at the front side (30a) and the back side (30b) of the adsorption filter plate, and wherein the carrier (4) comprises a planar front side (4a) in which a recess (5) is formed, wherein the sensing element (10) is arranged in said recess (5), and wherein the recess (5) comprises said opening (50) that extends in the plane of the planar front side (4a) of the carrier (4), wherein the back side (30b) of the adsorption filter plate (30) is glued to the front side (4a) of the carrier (4) such that a gas-tight seal is established between said material (3) and the carrier (4), so that the gas to be detected can only diffuse via said body (2) through the adsorption filter plate to reach the sensing element, and wherein said body (2) covers said opening (50) of the recess (5) of the carrier (4).

2. The sensor device (1) according to claim 1, characterized in that said body (2) comprises a diameter (D) in the range from 0.5 mm to 3 mm, or from 1 mm to 2 mm.

3. The sensor device (1) according to claim 1, characterized in that said adsorption filter (30) comprises merely a single body (2) of said molecular sieve material.

4. The sensor device according to claim 1, characterized in that said body (2) is one of: a bead, a section of a bead, a pellet, and a plate.

5. The sensor device according to claim 1, characterized in that the molecular sieve material is one of or comprises one of: a zeolite, a silica gel, clay, activated carbon, a polymer adsorbent, an aromatic polyimide, polyether ether ketone (PEEK), a perfluoropolymer, poly(2,6-diphenylphenylene oxide), and cellulose acetate.

6. Method for producing a sensor device, wherein a plurality of bodies (2) formed out of a molecular sieve material is arranged in a two-dimensional plane, wherein a free space between the bodies (2) is filled with a material (3) that is cured, wherein an adsorption filter plate (30) is formed in which the bodies (2) are embedded in said material (3) and each body (2) extends from a front side (30a) of said adsorption filter plate (30) to a back side (30b) of said adsorption filter plate (30), and wherein each body (2) is arranged in front of an associated sensing element (10) for forming a corresponding number of sensor devices (1) by one of:
separating said adsorption filter plate into a plurality of adsorption filter plate sections, wherein each section comprises one of said bodies, and arranging each of said adsorption filter plate sections on an associated carrier comprising a sensing element for forming a corresponding sensor device,
separating said adsorption filter plate into a plurality of adsorption filter plate sections, wherein each section comprises one of said bodies, and arranging each of said adsorption filter plate sections on the same carrier comprising a corresponding number of sensing elements so that each body is arranged in front of an associated sensing element, and separating the carrier with the attached adsorption filter plate sections into a plurality of individual sensor devices each comprising a body and a sensing element,
arranging said adsorption filter plate on a single carrier comprising a corresponding number of sensing elements so that each body is arranged in front of an associated sensing element, and separating the single carrier with the attached adsorption filter plate into a plurality of individual sensor devices each comprising a body and a sensing element.

7. Method for producing a sensor device, wherein a plurality of bodies (2) formed out of a molecular sieve material is arranged on a single carrier (4) that comprises a plurality of sensing elements (10) so that each body (2) is associated to one of the sensing elements (10), wherein a free space between the bodies (2) is filled with a material (3) that is cured, wherein an adsorption filter plate (30) is formed that is connected or glued to the single carrier (4), and wherein the carrier (4) with the attached adsorption filter plate (30) is separated into a plurality of individual sensor devices (1).

8. Method for producing a sensor device, wherein a plate-shaped body formed out of a molecular sieve material is arranged on a single carrier (4) that comprises a plurality of sensing elements (10), wherein molecular sieve material of the plate-shaped body (2) is removed around each sensing element (10) to form separate adsorption filter bodies (2), wherein each adsorption filter body (2) is associated to one of the sensing elements (10), and wherein a free space between said bodies (2) is filled with a material (3) that is cured to seal the respective adsorption filter body (2) to the carrier (4), and wherein the carrier (4) with the attached adsorption filter bodies is separated into a plurality of individual sensor devices (1).

* * * * *